United States Patent
Ring et al.

(10) Patent No.: US 6,354,406 B1
(45) Date of Patent: Mar. 12, 2002

(54) SAFETY ARRANGEMENT FOR A CABLE-SUPPORTED COMPONENT OF A MEDICAL DEVICE

(75) Inventors: Mario Ring, Bayreuth; Peter Rauh, Schnabelwaid; Alfred Ott, Immenreuth, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/597,804

(22) Filed: Jun. 19, 2000

(30) Foreign Application Priority Data

Jun. 30, 1999 (DE) .......................................... 199 30 123

(51) Int. Cl.⁷ ................................................. B60T 1/00
(52) U.S. Cl. ...................... 188/2 D; 187/348; 187/361; 188/8; 188/38.5; 188/43; 188/129
(58) Field of Search ................................. 187/348, 361; 188/8, 33, 35, 38, 38.5, 41, 43, 62, 2 D, 74, 128, 129; 104/112, 139, 140

(56) References Cited

U.S. PATENT DOCUMENTS

| | | | | |
|---|---|---|---|---|
| 124,592 A | * | 3/1872 | Klee | 187/246 |
| 229,203 A | * | 6/1880 | Thayer | 187/361 |
| 676,831 A | * | 6/1901 | Young | 187/349 |
| 1,268,260 A | * | 6/1918 | Matthews | 187/361 |
| 2,507,046 A | * | 5/1950 | Pearce | 188/369 |
| 2,561,060 A | * | 7/1951 | Lancaster | 188/362 |
| 3,645,519 A | * | 2/1972 | Schwarz et al. | 187/348 |
| 3,872,949 A | * | 3/1975 | Snyder | 188/189 |
| 3,941,353 A | | 3/1976 | Hack | |
| 4,444,293 A | * | 4/1984 | Paul et al. | 187/87 |
| 4,658,669 A | | 4/1987 | Nishikawa | |
| 5,040,644 A | * | 8/1991 | Turczyn et al. | 188/166 |
| 5,899,401 A | | 5/1999 | Reimann et al. | |
| 6,158,554 A | * | 12/2000 | Ferrari | 187/348 |
| 6,170,403 B1 | * | 1/2001 | Behringer | 104/59 |

* cited by examiner

Primary Examiner—Robert J. Oberleitner
Assistant Examiner—Devon Kramer
(74) Attorney, Agent, or Firm—Schiff Hardin & Waite

(57) ABSTRACT

In a safety arrangement of a cable-supported component of a medical device that can be adjusted via a cart at a column, a force acts on the cable via at least one clamping lever that is adjustably supported at the cart, and the cart is free for purposes of adjustment along the column given action of the force, and the clamping lever is moved such that it blocks displacement of the cart relative to the column when the force is reduced.

7 Claims, 5 Drawing Sheets

SAFETY ARRANGEMENT FOR A CABLE-SUPPORTED COMPONENT OF A MEDICAL DEVICE

BACKGROUND OF THE INVENTION

1. Field of the Invention

The present invention is directed to a safety arrangement for a cable-supported component of a medical device, and in particular to such a safety arrangement which arrests the component and prevents displacement thereof in the event of a cable breakage.

2. Description of the Prior Art

German PS 196 35 236 discloses a weight counterbalance device, particularly for a medical radiographic device, wherein a spring, is connected to oppose rotation of a drum on which a cable is wound, so that the spring exerts a force on the cable, which force counteracts the weight of a component, connected to the cable, of a medical device. This equilibration device can be allocated to a telescoping column that is guided at the ceiling and has an X-radiator arranged at its lower end. The equilibration device also has a further spring element and a further cable that act on separate safety means, which prevent a displacement of the X-radiator if the primary spring or the primary cable breaks, so that the X-radiator does not unimpededly fall by gravity on an obstacle or in the worst case, so as to even hit a person. The safety means has detent pawls which engage the housing of the cable drum, for example, in the event of a breakage.

German PS 36 21 565 describes a vertically adjustable holding device with a base block that can be moved in a groove of a carrying arm for a device component, and with a means for fixing and releasing the base block in the groove. The means for fixing and releasing has two swivel arms that each have a brake shoe at their ends. At the other end, each swivel arm is freely pivotably connected to a shaft. A mechanical operating element that engages the shaft, in the form of a rocker arm or an adjustment bar, cooperates with the shaft such that it can be vertically displaced. The base block can be fixed or released in the groove by actuating the operating element to rotate the shaft, whereby the brake shoes are latched in the groove or are released.

German OS 23 52 836 describes a clamping device for fixing two machine parts that can be spatially displaced relative to one another. The clamping device has a number of prestressed clamping bodies. The clamping bodies cooperate with covering walls, which, when a force acts upon the clamping bodies, are pushed outwardly in order to achieve a latching of the clamping device, in a groove, for example. The clamping device can be fashioned in a self-locking manner.

SUMMARY OF THE INVENTION

An object of the present invention is to provide a safety arrangement for a cable-supported component of a medical device that can be adjusted via a cart at a column such that, in a reliable manner, it prevents displacement of the cart when the cable and/or a spring breaks, (if present) for example.

The above object is achieved in accordance with the principles of the present invention in a medical device having a column in which a rider block is movable, and at least one clamping lever connected to a cable, the cable supporting a medical device component at an opposite end and the clamping lever being movably mounted at the rider block, so that when a force acts on the cable the rider block is freely movable within the column so as to allow adjustment of the position of the cable-supported component, and wherein the clamping lever is mounted to the rider block so as to prevent displacement of the rider block relative to the column when the force acting on the cable is reduced or removed.

An advantage of the invention is that a force acts on at least one clamping lever that is adjustably at the cart via a cable, for example, so that given action of the force, the cart is free for purposes of adjusting along the column and whereby, given reduction of the force, the clamping lever is automatically deployed such that it blocks the displacement of the cart relative to the column. Such a safety arrangement is uncomplicated in the construction, since only one clamping lever is provided via which a displacement of the cart can be blocked. Besides, the clamping lever is effective regardless of whether the cable or spring used for purposes of compensating the weight of the component breaks. Therefore, double safety measures need not be provided, as in the prior art, since the safety arrangement is self-locking.

It is especially advantageous when the force acts on the cable at the clamping lever and when the force originates from an equilibration arrangement for compensating the weight of the component and the cart. Therefore, a safety arrangement is created that blocks displacement of the cart via a clamping lever given no action of the force of the equilibration arrangement, as occurs when the cable breaks, for example.

It is also advantageous for the force to be conducted to the clamping lever via a manually operated element, since the user, by applying a force, thus can displace the cart and the component, and a blocking of the displaceability of the cart ensues via the manually operable element when a force is present.

It is advantageous for the clamping lever to effect blocking of displacement of the cart in a spring-weighted manner, since the response of the clamping lever can be adjusted depending on the spring loading (biasing).

In an embodiment wherein two clamping levers are provided which engages the cable, a symmetrical blocking of displacement of the cart ensues and the forces of the blocking are also distributed via both clamping levers.

For achieving a lever action, it is advantageous for each clamping lever to be pivoted around respective pivot axles, with the cable engaging a cable arm or clamping arm of the clamping lever.

In a further embodiment the clamping levers have a common spring element.

A compact structure of the safety arrangement in an embodiment wherein from the clamping arm and the cable arm of the clamping levers forming an angle toward one another.

Here, it is also advantageous for the clamping arms have a common pivot axle, around which they can be pivoted.

DESCRIPTION OF THE PREFERRED EMBODIMENTS

The same elements are identified with the same reference numbers in the figures.

Figure 1:
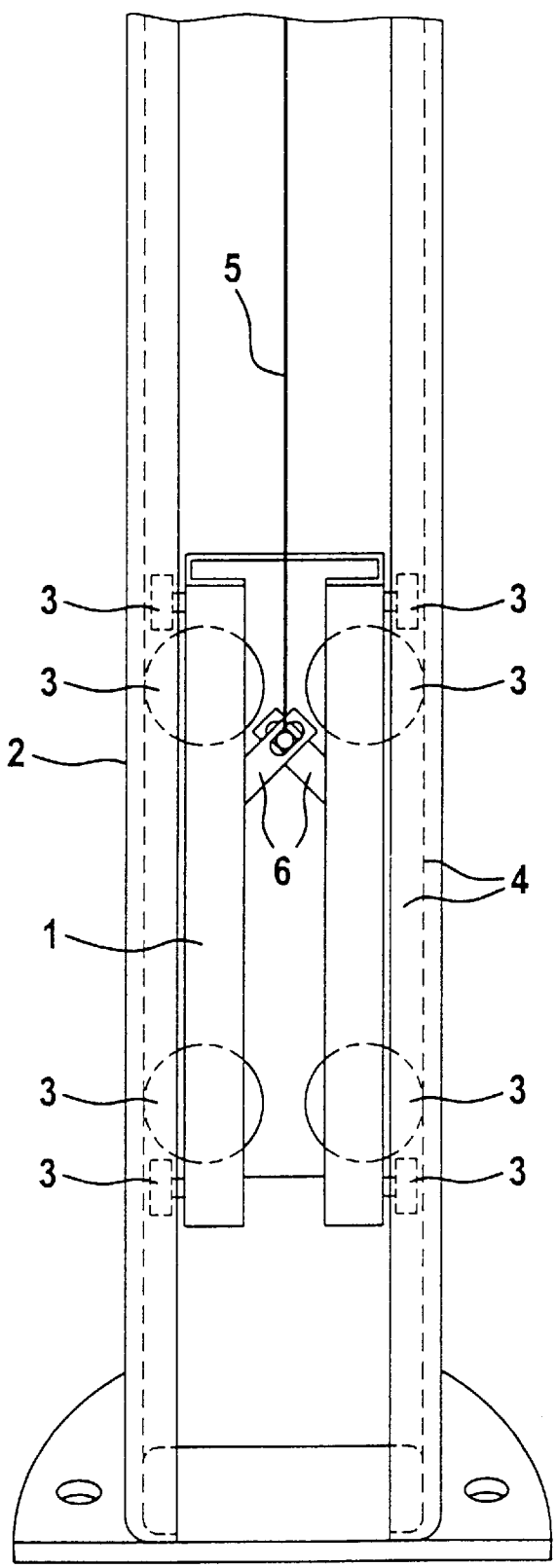
FIG. 1 shows an exemplary embodiment of the inventive safety arrangement for a component of a medical device that can be adjusted via a cart at a column.

As shown in FIG. 1, a cart 1 can be adjusted along a column 2. For this purpose, the cart 1 has wheels 3, which are in connection with guides 4 that are provided at the column 2. A component of a medical device, such as an X-ray emitter, a radiation receiver, a support device for an examination subject and/or a display can be supported at the cart 1. In order to compensate the weight of this component and to enable a displacement of the cart 1, a cable 5 engages the cart 1, the cable 5 being in connection with a mechanical arrangement or an electromechanical arrangement or a counterweight, to produce a counterforce to the weight of the supported component. In the framework of the invention, the cable 5 can alternatively be fashioned as a belt, such as a toothed belt. For preventing an undesired displacement of the cart 1 and therefore of the supported component, if the cable 5 breaks, an inventive safety arrangement is provided that prevents the displacement of the cart 1 if the cable 5 breaks. According to a version of the invention, the cable 5 engages at least one clamping lever 6, which, if the cable 5 breaks, is either deployed by its own weight or is displaced in a spring-biased manner such that it blocks displacement of the cart 1 relative to the column 2. In the exemplary embodiment according to FIGS. 2, 4 and 5, two clamping levers 6 are provided that can be respectively rotated around an allocated rotational axis 7 (according to the FIGS. 2 and 5). For effecting an optimally compact structure of the safety arrangement, it is advantageous when the clamping arm 8 and the cable arm 9 of the clamping lever 6 form an angle toward one another. According to FIG. 2, the cable 5 and a spring element 10 the cable arm 9, the spring element 10 being arranged common with the clamping levers 6. Given a break of the cable 5, the clamping levers 6 are adjusted by means of the force of the spring element 10 such that the clamping arms 8 engage sides 11 of the column 2 in a clamping (frictional) fashion, which sides 11 are opposite to one another. This prevents a displacement of the cart 1. The material of the clamping arms 8 that generate the clamping or braking is selected such that is has a high coefficient of friction with the material of the column 2. Preferably, the clamping levers 6 at the cart 1 are arranged such that the clamping arms 8 do not engage at the guides 4 for the wheels 3, so that these are not damaged given deployment of the safety arrangement. In the framework of the invention, the clamping levers 6 can cooperate with recesses or projections at the column 2 for effecting the blocking of displacement of the cart 1. Further, the clamping arms 6 can be fashioned with a brake lining or hard rubber at least the surfaces facing the sides 11, since a particularly high coefficient of friction therefore results in connection with a column 2 that is composed of steel or aluminum.

Figure 3:
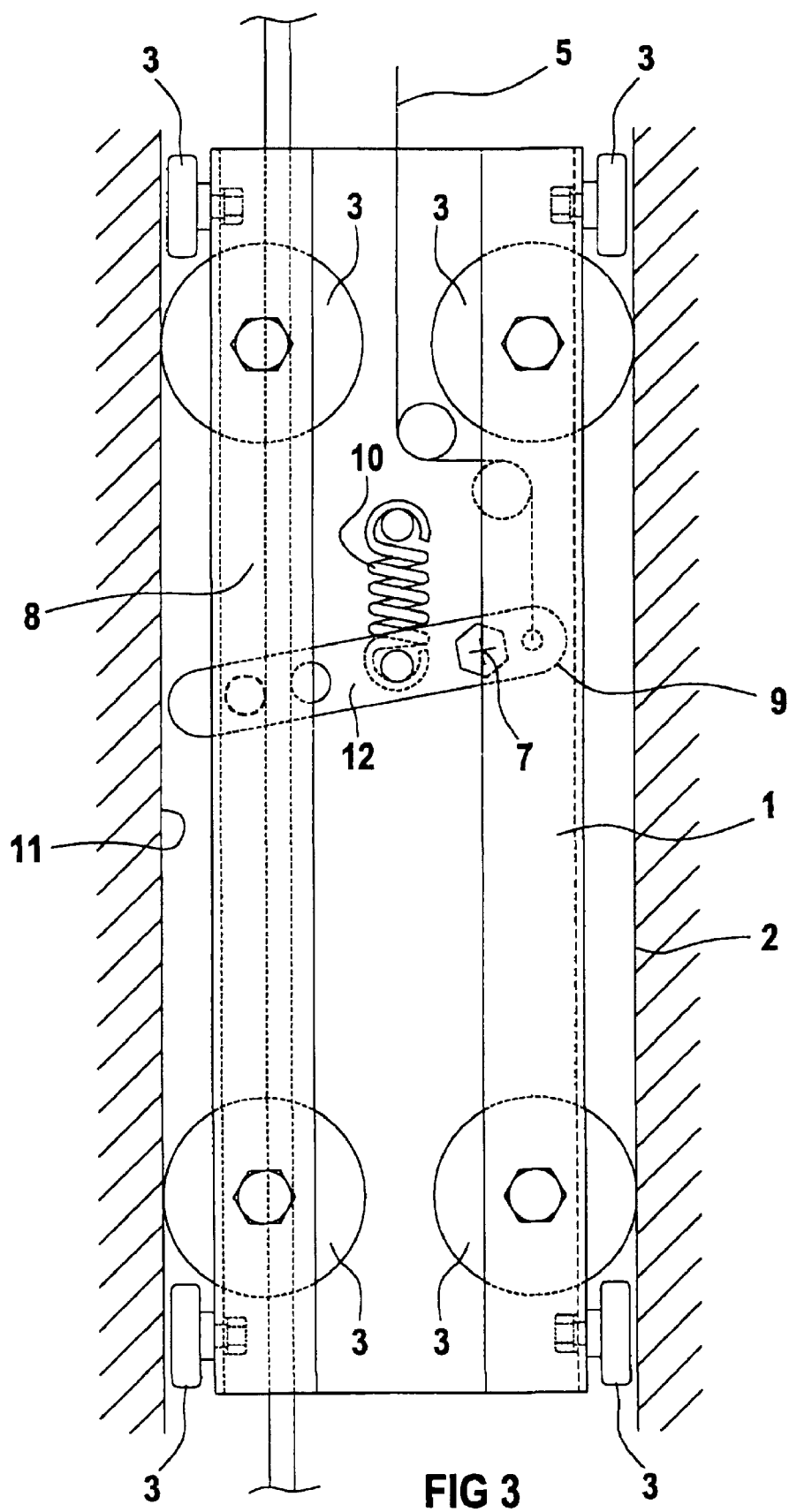

FIG. 3 shows a version of the inventive safety arrangement, which has only a single clamping lever 12 that can be pivoted around a rotational axis 7. The cable 5 also engages a rope arm 9. Given a breakage of the cable 5, the one single clamping lever 12 is biased by means of the spring element 10, and is pivoted around the rotational axis 7, so that the clamping arm 8 enters into engagement with the allocated side 11 of the column 2, producing a braking effect.

Figure 4:
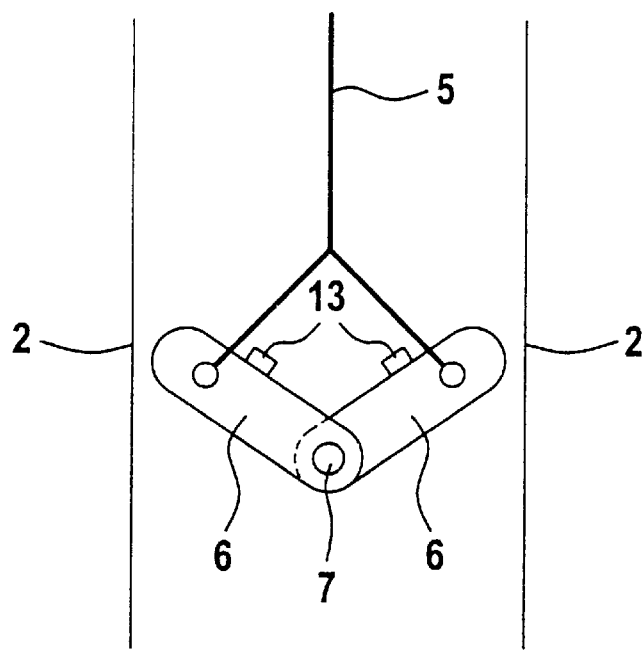

As shown in FIG. 4, a further exemplary embodiment of an inventive safety arrangement has two clamping levers 6, which, at one end, can be pivoted around a common rotational axis 7. In this exemplary embodiment, the cable 5 engages the clamping levers 6, which are supported at support elements 13. Due to gravity, these clamping levers 6 drop if the cable 5 breaks, so they are pivoted around the rotational axis 7 and, at ends opposite to the rotational axis 7, engage the column 2 for effecting the braking. A spring element can be foregone in this embodiment.

Figure 2:
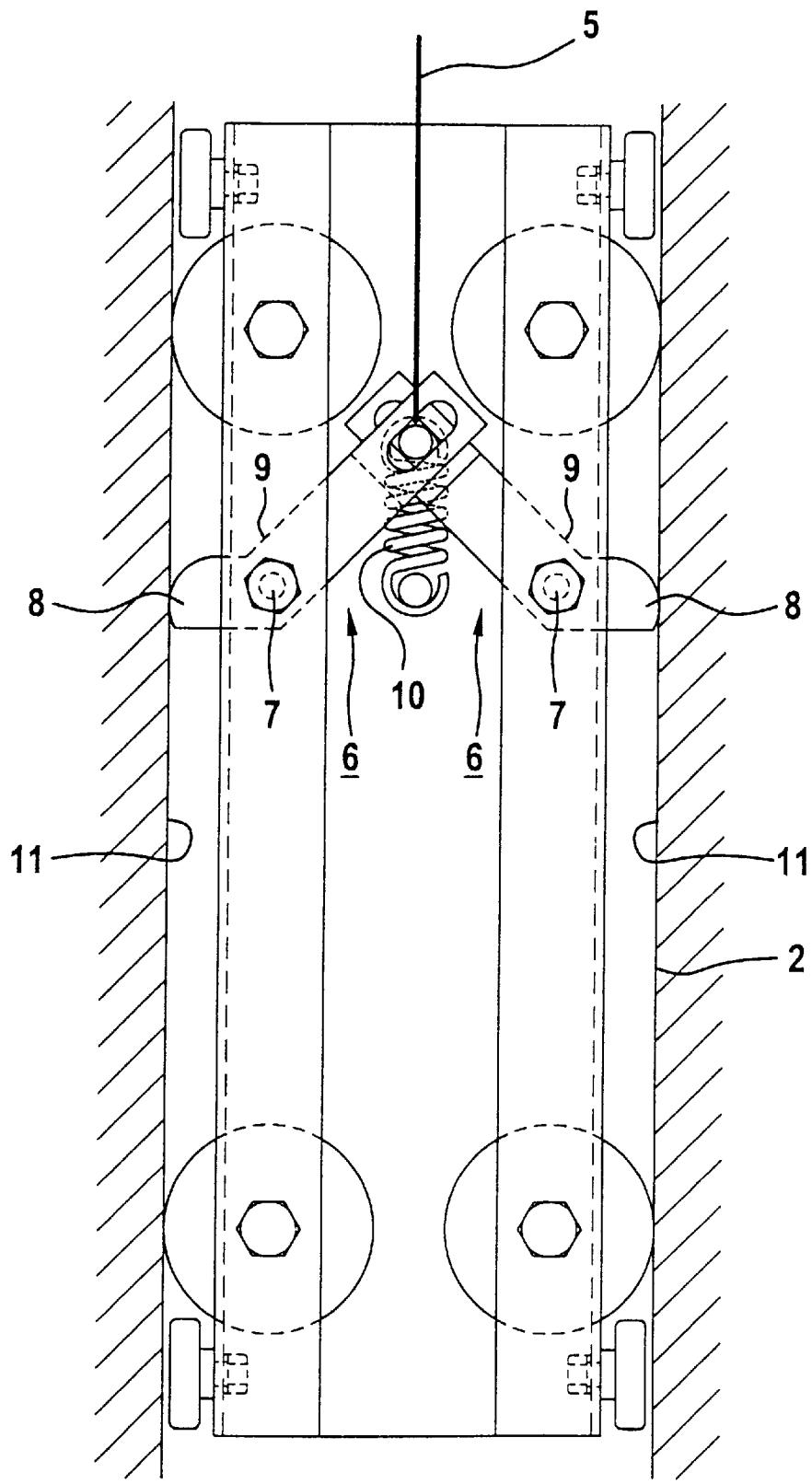
FIGS. 2–5 respectively show further exemplary embodiments of the inventive safety arrangement.

In the embodiments of the clamping levers 6 according to FIGS. 2 through 4, the ends that are closer to the sides 11 of the column 2 are in a rounded manner, so that the clamping (braking) is reliable and also is increased.

Figure 5:
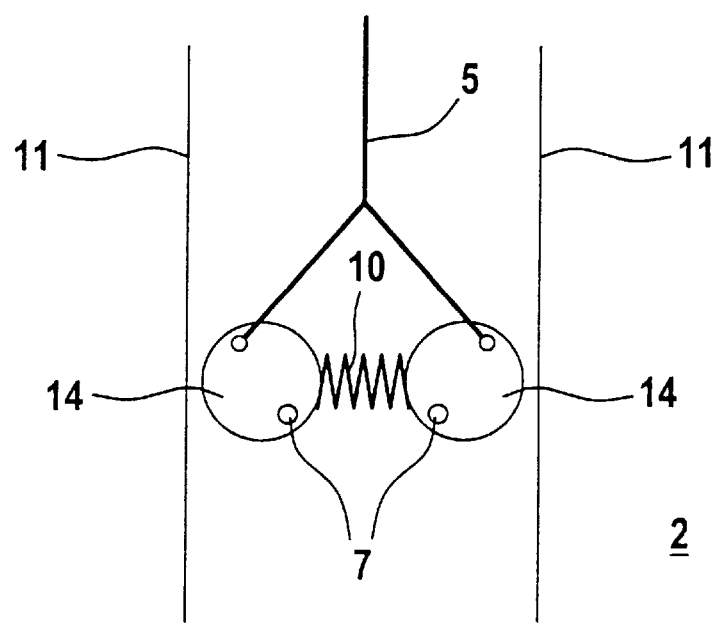

As shown in FIG. 5, the clamping levers can be replaced by clamping discs 14, each of which is eccentrically rotatable around a rotational axis 7. These clamping discs 14 can be respectively pivotable around separate rotational axes 7 or around a common rotational axis 7. Further, these clamping discs 14, by gravity or by the force of a spring arm, can engage the sides 11 of the column 2 for effecting the braking given breakage of the cable 5.

Figure 6:
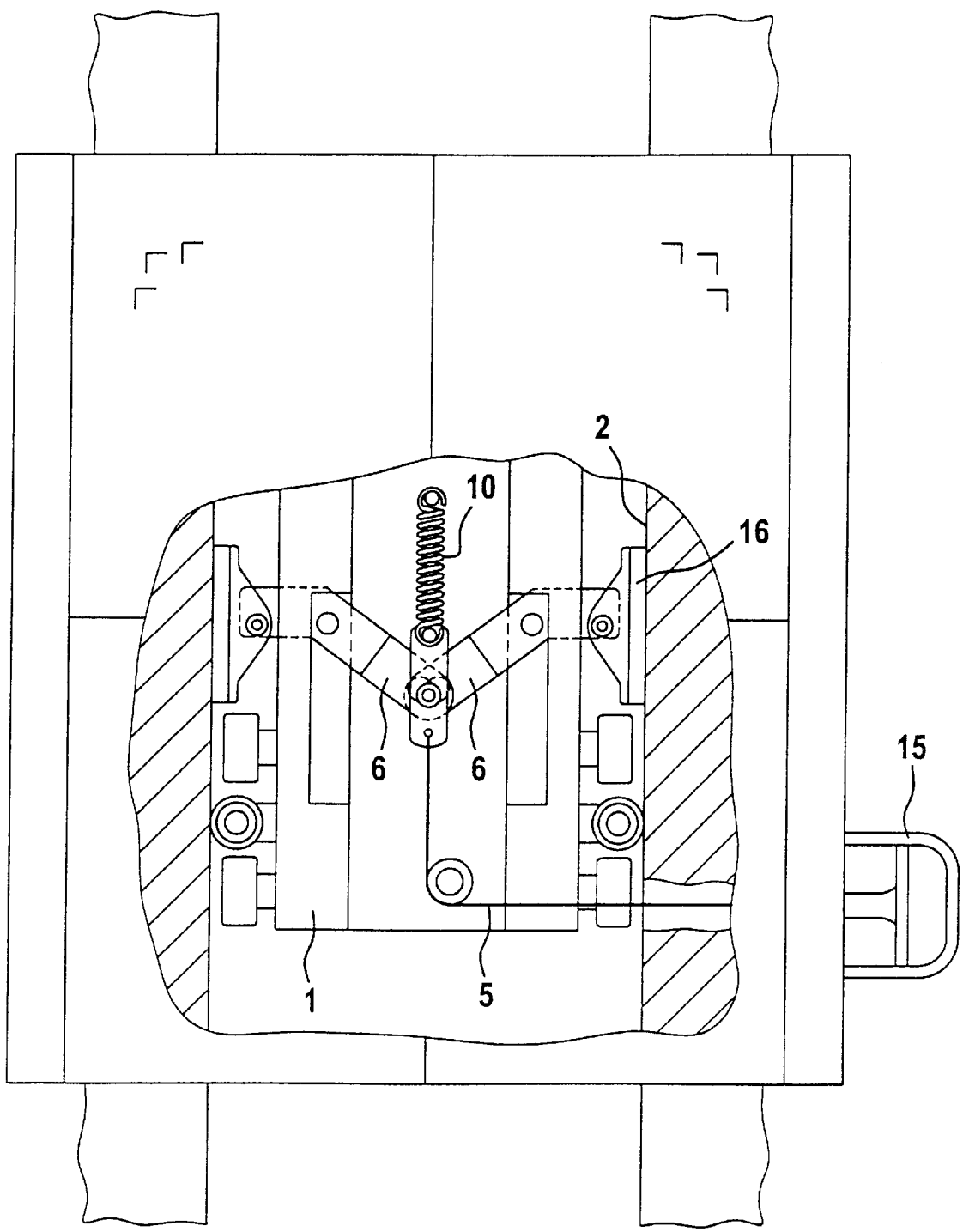
FIG. 6 shows another exemplary embodiment of the inventive safety arrangement for a component of a medical device that can be adjusted via a cart at a column, with a manually operable element.

In another exemplary embodiment of an inventive safety arrangement according to FIG. 6, a manually operable element 15 is provided at the cart or at the displaceable component, which can be fashioned as an X-ray film holder or as a radiation detector, for example. This manually operable element 15 is in connection with the clamping lever 6 via the cable 5 or via a hydraulic means, for example. In the shown status, a force—originating from the spring element 10—acts on the clamping lever or clamping levers 6, so that their clamping surfaces 16 at their ends are in engagement with the column 2. The clamping surfaces 16 are preferably fashioned with a brake lining for generating a high frictional force in combination with the column 2. For neutralizing the brake force via the clamping levers 6, the manually operable element 15 is displaced in a direction away from the cart 1, so that a force ensues via the cable 5 on the clamping lever(s) 6 for a displacement counter to the spring force. Hereby, the clamping surfaces 16 are displaced in a direction away from the column 2, so their friction with the column 2 decreases or is canceled. As a result, the cart 1 can be freely displaced and therefore the component as well. When the force at the manually operable element 15 is reduced or canceled, a displacement of the clamping surfaces 16, which is produced by spring force, ensues via the clamping levers 6 in the direction of the column 2, so the displaceability of the cart 1 is blocked. In this exemplary embodiment, the safety arrangement explained in the previous figures can also be employed, particularly concerning the fashioning of the clamping levers.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a medical device having a component supported by a cable, said cable being guided within a column, the improvement of a safety arrangement comprising:

a rider block movable within said column;

two clamping levers mounted to said rider block at a pivot bearing around which each of said clamping levers is pivotable, each of said clamping levers having a cable arm to which said cable is connected; and said two clamping levers being mounted to said rider block to maintain a position relative to said column allowing said rider block to move relative to said column as long as a force acts on said clamping levers via said cable, and for moving to a position which blocks movement of said rider block relative to said column when said force acting on said clamping levers via said cable is reduced.

2. The improvement of claim 1 wherein said clamping levers are mounted to said rider block with a spring loading which displaces said clamping levers when said force is reduced.

3. The improvement of claim 1 wherein each of said clamping levers has a braking arm, said cable engaging the respective braking arms of said clamping levers.

4. The improvement of claim 1 further comprising a common spring element connected to said clamping levers for displacing said clamping levers when said force is reduced.

5. The improvement of claim 1 further comprising a weight compensation device which produces said force acting on said cable.

6. The improvement of claim 1 further comprising a manually operable source for producing said force.

7. In a medical device having a component supported by a cable, said cable being guided within a column, the improvement of a safety arrangement comprising:

a rider block movable within said column;

a clamping lever having a braking arm and a cable arm disposed at an angle relative to each other, said cable engaging said cable arm of said clamping lever; and said clamping lever being mounted to said rider block to maintain a position relative to said column allowing said rider block to move relative to said column as long as a force acts on said clamping lever via said cable, and for moving to a position which blocks movement of said rider block relative to said column when said force acting on said clamping lever via said cable is reduced.

* * * * *